(12) United States Patent
Grannell et al.

(10) Patent No.: US 9,572,933 B2
(45) Date of Patent: Feb. 21, 2017

(54) EXTRAVASATION DETECTION APPARATUS AND METHODS

(71) Applicants: Shawn Grannell, Ann Arbor, MI (US); Donald E. Gillespie, Ann Arbor, MI (US)

(72) Inventors: Shawn Grannell, Ann Arbor, MI (US); Donald E. Gillespie, Ann Arbor, MI (US)

( * ) Notice: Subject to any disclaimer, the term of this patent is extended or adjusted under 35 U.S.C. 154(b) by 15 days.

(21) Appl. No.: 14/491,316

(22) Filed: Sep. 19, 2014

(65) Prior Publication Data

US 2016/0082185 A1    Mar. 24, 2016

(51) Int. Cl.
*A61M 5/168* (2006.01)
*A61M 39/28* (2006.01)
*A61M 25/06* (2006.01)
*A61M 5/158* (2006.01)

(52) U.S. Cl.
CPC .... *A61M 5/16836* (2013.01); *A61M 25/0693* (2013.01); *A61M 39/28* (2013.01); *A61M 39/285* (2013.01); *A61M 2005/1588* (2013.01)

(58) Field of Classification Search
CPC ...... A61M 2005/1588; A61M 5/16859; A61M 25/0693; A61M 39/287; A61M 39/286; A61M 5/16836; A61M 5/5086; A61M 39/285; A61M 39/28; A61M 5/14228; A61M 5/14232
USPC .......................................................... 251/6
See application file for complete search history.

(56) References Cited

U.S. PATENT DOCUMENTS

| 1,330,523 | A | * | 2/1920 | Evitts | A61M 39/286 251/6 |
| 3,135,259 | A | * | 6/1964 | Evans | A61M 39/286 137/561 R |
| 3,893,468 | A | * | 7/1975 | McPhee | A61M 39/286 137/1 |
| 4,164,223 | A | | 8/1979 | Munib | |
| 4,320,889 | A | * | 3/1982 | Genese | A61M 39/285 251/6 |
| 4,367,754 | A | | 1/1983 | Akhavi | |
| 4,406,440 | A | * | 9/1983 | Kulle | A61M 39/286 251/6 |
| 4,492,538 | A | | 1/1985 | Iwata | |
| 4,552,599 | A | * | 11/1985 | Masuda | B21C 37/042 156/50 |
| 4,662,599 | A | * | 5/1987 | Attermeier | A61M 39/286 251/4 |
| 4,856,755 | A | * | 8/1989 | Clarke | A61M 39/286 251/4 |
| 5,257,770 | A | * | 11/1993 | Grove | A61M 39/286 251/297 |
| 5,279,572 | A | | 1/1994 | Hokama | |
| 5,334,141 | A | | 8/1994 | Carr et al. | |
| 5,423,746 | A | | 6/1995 | Burkett et al. | |

(Continued)

*Primary Examiner* — Bhisma Mehta
*Assistant Examiner* — Jenna Zhang
(74) *Attorney, Agent, or Firm* — John G. Posa; Belzer PC

(57) ABSTRACT

Described herein is an extravasation tester that pinches an infusion line closed between a wheel and a platen, and then peristaltically withdraws fluid into the infusion line as the wheel is rolled away from a puncture site. Extravasation is determined to have occurred if little or no blood appears in a sight chamber positioned near the puncture site when a test fluid is withdrawn into the infusion line from the puncture site.

5 Claims, 8 Drawing Sheets

(56) References Cited

U.S. PATENT DOCUMENTS

| | | |
|---|---|---|
| 5,871,465 A | 2/1999 | Vasko |
| 5,954,668 A | 9/1999 | Uber, III et al. |
| 6,422,529 B1 | 7/2002 | Adelberg |
| 6,929,236 B1* | 8/2005 | Height ................. A61M 39/286 137/553 |
| 8,202,253 B1 | 6/2012 | Wexler |
| 8,313,081 B2 | 11/2012 | Adelberg |
| 8,320,999 B2 | 11/2012 | Ono |
| 8,348,896 B2 | 1/2013 | Wagner |
| 2007/0112329 A1 | 5/2007 | Sage |
| 2007/0272886 A1* | 11/2007 | Abe .................... A61M 39/286 251/6 |
| 2008/0029721 A1* | 2/2008 | Miyahara ............ A61M 39/287 251/6 |
| 2009/0247964 A1* | 10/2009 | Kitani ................... A61M 39/28 604/250 |
| 2011/0319820 A1* | 12/2011 | Teoh ................ A61M 25/0014 604/122 |
| 2013/0310743 A1 | 11/2013 | Yagi et al. |

* cited by examiner

EXTRAVASATION DETECTION APPARATUS AND METHODS

FIELD OF THE INVENTION

The present disclosure relates to extravasation detection. An extravasation tester withdraws fluid back into an intravenous infusion line in conjunction with performing an extravasation test. The extravasation test is "passed" if a richly dark density of blood appears in a sight chamber positioned near a puncture site when a test fluid is withdrawn into the sight chamber from the puncture site. The extravasation test is "failed" if little or no blood appears in the sight chamber when the test fluid is withdrawn into the sight chamber from the puncture site.

BACKGROUND OF THE INVENTION

Patients can be severely injured when fluids that are intended for intravenous delivery are delivered outside a targeted vein. Possible consequences of prolonged delivery of an infused fluid outside the targeted vein include irritation, tissue necrosis, compartment syndrome, disfigurement, loss of limb function, amputation, and even death of the patient. Extravasation occurs when the outlet of a cannula is misplaced or becomes dislodged to a region outside the vein. Extravasation refers herein to improper placement or movement of the outlet of an intravenous cannula to a region outside the targeted vein, or delivery of a fluid that is intended for intravenous delivery outside the targeted vein.

Various methods are known to the art for detecting extravasation in an infusion system. Such tests can be employed for minimizing delivery, outside a targeted vein, of fluids intended for delivery within the targeted vein. If extravasation is detected, then the flow of delivered fluid can be stopped when the faulty condition becomes known.

In one method of detecting the proper placement of a cannula during an infusion, the DC component of the pressure is monitored in an infusion line. Proper placement of the cannula in a vein is detected when the pressure in the infusion line tracks the DC component of the pressure in the vein. Extravasation is determined to have occurred if the monitored pressure occurs outside a prescribed pressure range. However, this method suffers from the possibility of failure to detect extravasation, because an apparently proper pressure can be produced while the cannula is outside the vein, resulting in significant accumulation of extravasated fluid and possible injury when the infusion is continued under the undetected faulty condition. Furthermore, the DC pressure method requires sophisticated electronics, which may be unavailable in some emergency situations such as accident sites and battlefields, unavailable at severely budget-constrained clinics, or which may be unsuitable for flowing vesicant or cytotoxic medicines, for very low flow applications, or for any other applications in which it is preferred not to use a powerhead for infusing a fluid. A powerhead is a powered pump that positively actuates forced delivery in an infusion line.

Another extravasation detection method uses the AC component of the vein pressure. Both veins and arteries have a pulsing AC pressure component. The AC pressure component can be detected as either a variation in pressure or a variation in flow in an infusion line, according to U.S. Patent Application Publication No. 2007/0112329. The pulsing AC pressure is detected in the infusion line if the cannula is properly placed in the vein, and not detected if extravasation has occurred. If a pulse is not detected for a few seconds at any time after the start of an infusion, then extravasation is determined to have occurred. However, like the DC pressure method, the AC pressure method requires sophisticated electronics which may be unavailable or unsuitable for the same above listed reasons.

Numerous references disclose extravasation detection with infrared, RF, microwaves, ultrasound, light, pressure response to a test injection, or changes in temperature. These methods require sophisticated electronics and many of them involve probes which are applied separately from the infusion line. Extravasation is inferred from a measured change that is a secondary consequence of accumulation of extravasated fluid. Assumptions are made and relied upon as to how tissue properties will change when a delivered fluid accumulates outside a vein, and significant quantities of extravasated fluid may accumulate as the infusion is continued under an undetected faulty condition if these assumptions fail.

U.S. Patent Application Publication No. 2013/0310743 discloses a test that detects extravasation by monitoring for entry of blood near the cannula when the flow of delivered fluid is momentarily reversed by a finger-type powerhead. However, in some applications, it is preferred not to use a powerhead, such as for intravenous delivery of vesicant or cytotoxic medicines, for medicines that are delivered at a very low flow rate, or for any other medicine or circumstance in which forced delivery of the medicine is contraindicated.

In one commonly used extravasation test, an infusion line is backflowed with a syringe. A syringe is connected in flow communication with the infusion line between a puncture site and a point in the infusion line at which the flow has been restricted or shut off. Proper placement of the cannula is detected if blood flows back into the infusion line from the puncture site when the syringe's plunger is pulled back. This method requires the syringe or other extra equipment not already present on the infusion line, which must be supplied for performing the test. Repeated testing with this method consumes many syringes, the total of which may be expensive, and the test itself requires significant effort to perform, all of which present a deterrent of using this method to check or monitor proper placement of the cannula. Furthermore, concerns are raised about sterility when a syringe or other additional equipment is placed in flow communication with an infusion line.

"Roller clamps" have been used for throttling the flow in an infusion line. The roller clamps shown in U.S. Pat. Nos. 6,422,529 and 8,313,081 have a wheel that pinches an infusion line against a bottom wall having a relief groove in order to throttle an adjustable, nonzero flow throughout the substantial length of the wheel's range of travel. The roller clamps shown in U.S. Pat. Nos. 6,422,529 and 8,313,081 do not aim to pinch the infusion line fully closed and then peristaltically withdraw fluid back into the infusion line by movement of the point of closure.

Based on the forgoing, there is a need for an extravasation tester that pinches an infusion line closed between a wheel and a platen, and then peristaltically withdraws fluid into the infusion line as the wheel is rolled away from a puncture site. Extravasation is determined to have occurred if little or no blood appears in a sight chamber near the puncture site when fluid is withdrawn into the infusion line from the puncture site.

SUMMARY OF THE INVENTION

Described herein is an extravasation tester used for performing an extravasation test. The extravasation tester pinches an intravenous infusion line's delivery tube closed between a wheel and a platen. The wheel pinches the delivery tube fully closed against the platen when the wheel is moved out of a free-flow region and into a tube-pinching region above the platen. Fluid is peristaltically withdrawn into the infusion line from a puncture site by movement of the point of tube closure between the wheel and the platen as the wheel is rolled on the delivery tube away from the puncture site. If a richly dark density of blood appears in a sight chamber positioned near the puncture site when the wheel is rolled away from the puncture site, then the extravasation test is said to be "passed", and the wheel may be returned to the free-flow region in order to resume the infusion. If little or no blood appears in the sight chamber when the wheel is rolled away from the puncture site, then the extravasation test is said to be "failed", and the delivery tube is left in a closed state until a corrective action is performed.

DETAILED DESCRIPTION OF THE INVENTION

Figure 1:
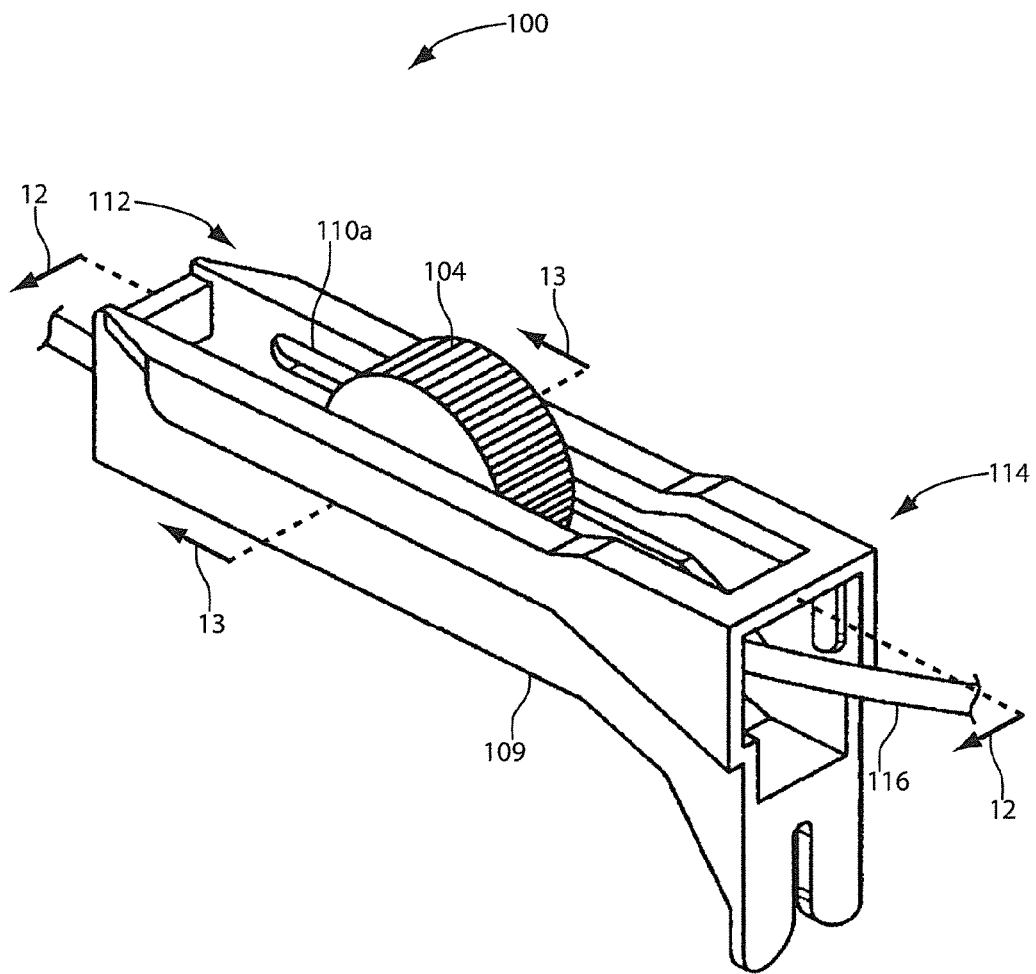
FIG. 1 is an overview of an extravasation tester.

FIG. 1 illustrates an overview of an extravasation tester 100. The extravasation tester 100 is mounted on a flexible, elastic or at least semi-elastic delivery tube 116. A wheel 104 is positioned over the delivery tube 116. The wheel 104 is movably captivated within a pair of opposing guide slots 110 that are formed in a frame 109, of which one of the slots 110a is visible in FIG. 1. Surfaces of the frame 109, facing the sides of the wheel 104, also prevent the wheel 104 from twisting out of the vertical plane, while allowing the wheel 104 to roll about its central axis and also allowing the wheel 104 to slide along the long dimension of the frame 109. Additional detail is shown in a cross-sectional view taken in the direction of arrow pair 12 in FIG. 2, and in a cross-sectional view taken in the direction of arrow pair 13 in FIG. 3.

The extravasation tester 100 uses an architecture that is very similar to the conventional architecture of the "roller clamps" that are used for throttling a nonzero flow. The extravasation tester 100 may be dyed, painted, or decaled with a unique color or pattern to distinguish it from otherwise similar-appearing devices having different functions, which may also be mounted elsewhere on the delivery tube 116. For example, a yellow and black striped "safety" pattern may be used, denoting the extravasation tester's 100 safety-related function.

The extravasation tester 100 has mirror symmetry about a vertical plane passing through the dashed lines adjacent each of the arrows in arrow pair 12 in FIG. 1. Paired components are numbered individually with numbers in the form of Xa and Xb, for example, 110a and 110b for the slots. In some of the figures, the paired components overlap exactly, such that individual components of the pair are not separately visible, in which case the pair is numbered with the same X that was used for the individual components Xa and Xb, for example, 110 for the pair of slots. Wherever there is a component Xa shown on one side of the plane of symmetry, there is an opposing component Xb on the other side, and vice versa. Each part and pair number is common to the same parts and pairs in all figures, although not all numbers appear in all figures, and the same parts and pairs may be drawn differently in different figures.

Figure 2:
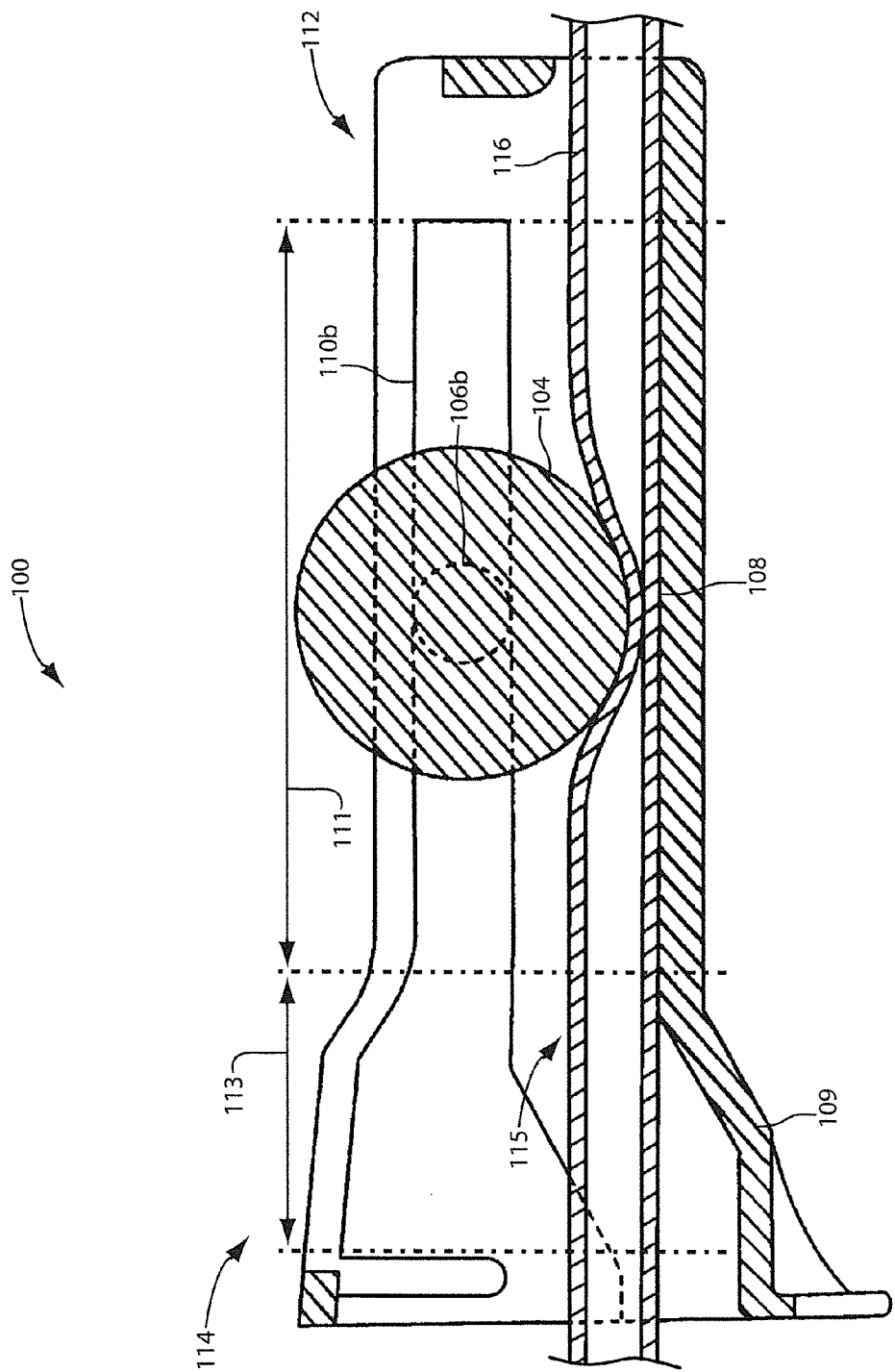
FIG. 2 is a cross-sectional view of the extravasation tester, taken in the direction of arrow pair 12 in FIG. 1.

FIG. 2 illustrates a cross-sectional view of the extravasation tester 100, taken in the direction of arrow pair 12 in FIG. 1. The frame 109 has a hollow bore 115 occupied by the delivery tube 116. The extravasation tester 100 has a free-flow region 113 and a tube-pinching region 111. Fluid is allowed to flow freely in the delivery tube 116 when axial post 106b of the wheel 104 is within the free-flow region 113. The frame 109 has a platen 108, against which the delivery tube 116 is pinched fully closed by the wheel 104 when post 106b is within the tube-pinching region 111. The platen 108 is the long and flat portion of the inner surface of the diagonally hatched bottom wall of the frame 109, facing toward the delivery tube 116 and spanning the tube-pinching region 111. Some of the outer surfaces of the frame 109 may be made rounded or triangular for additional strength. The frame 109 may be formed from one piece of injection molded plastic or 2 pieces which are welded, bonded, or otherwise joined at the plane of symmetry or elsewhere, or by other methods that are known to the art.

Although it is foreseen that a flow-throttling region may also be incorporated into the extravasation tester 100 within the free-flow region 113 or between the free-flow region 113 and the tube-pinching region 111 shown in FIG. 2, it is preferred to provide flow controlling apparatus separately from the extravasation tester 100, so that the flow setting need not be readjusted after a "passed" extravasation test is performed. This allows extravasation tests to be performed quickly and with minimal effort, such that a user is not deterred from repeatedly performing extravasation tests in setup or while monitoring, or whenever there is even a slight suspicion of a faulty condition. Most generally, a fluid in the delivery tube 116 is allowed to flow past the wheel 104 when post 106b is within the free-flow region 113, and fluid is not allowed to flow past the wheel 104 when post 106b is within the tube-pinching region 111.

The frame 109 also has a pair of opposing guide slots 110, of which one of the slots 110b is visible in FIG. 2. Post 106b slides within slot 110b in a direction that is parallel to the long dimension of the frame 109 as the wheel 104 is rolled on the delivery tube 116. The wheel 104 has a constant clearance above the platen 108, equal to twice a targeted wall thickness for the delivery tube 116 or slightly less than that. The point of tube closure, between the wheel 104 and the platen 108, is moved along the delivery tube 116 with the wheel 104 by rolling the wheel 104 on the delivery tube 116 in the tube pinching region 111, which also causes fluid in the delivery tube 116 to move peristaltically with the wheel 104. The platen 108 and/or the circumferential outer surface of the wheel 104 may be knurled or roughened, so that the delivery tube 116 is not allowed to slip on the platen 108, and the wheel 104 is not allowed to slip on the delivery tube 116, when post 106b is within the tube-pinching region 111. Knurling of the wheel 104 also minimizes slipping of a thumb or finger on the wheel 104 while a user moves the wheel 104. The user moves the wheel 104 while holding the frame 109 in one or both hands.

Figure 3:
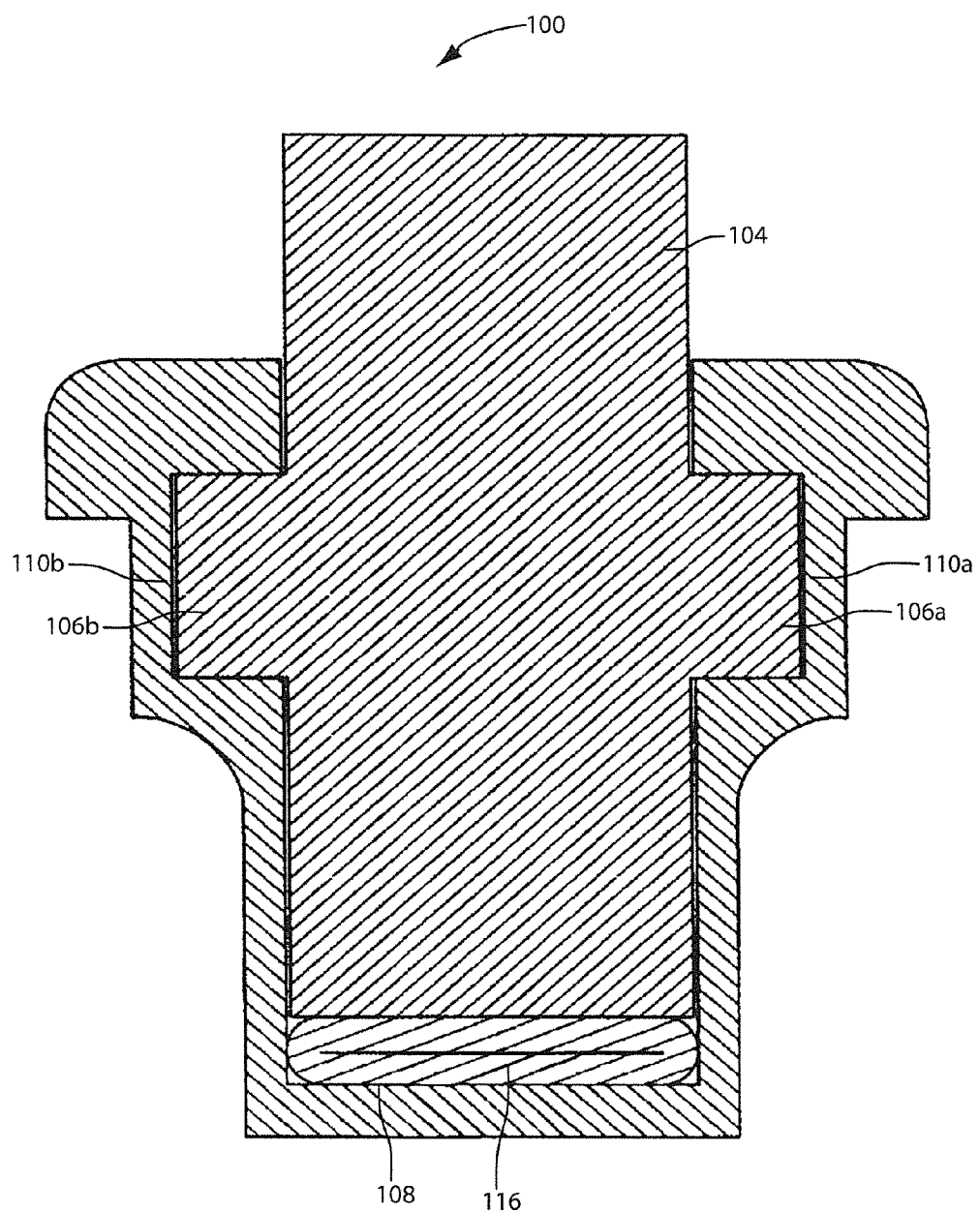
FIG. 3 is a cross-sectional view of the extravasation tester, taken in the direction of arrow pair 13 in FIG. 1.

FIG. 3 illustrates a cross-sectional view of the extravasation tester 100, taken in the direction of arrow pair 13 in FIG. 1. This view shows the delivery tube 116 pinched fully closed between the platen 108 and the circumferential outer surface of the wheel 104. The wheel 104 is held down against the delivery tube 116 by axial post 106a in slot 110a and by axial post 106b in slot 110b. The posts 106a and 106b slide in the slots 110a and 110b, respectively, in a direction that is perpendicular to the page of FIG. 3 when the wheel 104 is rolled on the delivery tube 116. The wheel 104 is thus translatable along the slots 110a and 110b. The opposing axial posts 106a and 106b are concentric with the wheel 104, and the centers of posts 106a and 106b define the central axis of the wheel 104, about which the wheel 104 is rotatable. Posts 106a and 106b and wheel 104 may be formed from a single piece of injection molded plastic.

Figure 4:
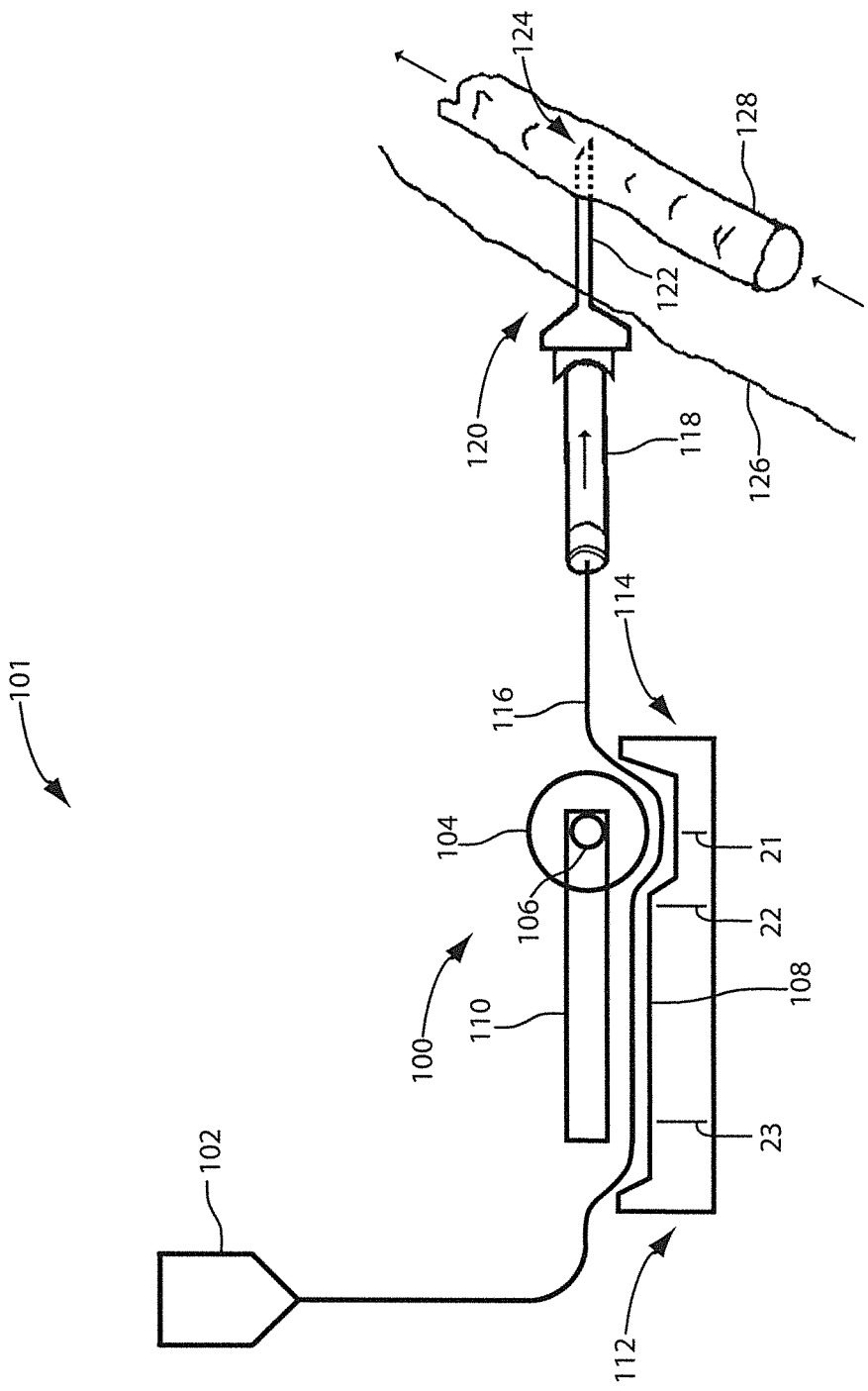
FIG. 4 is a schematic of an infusion system operating under a normal flow condition, the infusion system incorporating the extravasation tester.

FIG. 4 is a schematic illustrating an infusion system 101 operating under a normal flow condition, the infusion system 101 incorporating the extravasation tester 100. The small arrows indicate the direction of flow. The infusion system 101 also has an infusion line comprising a source of infused fluid 102, the delivery tube 116, a sight chamber 118, and a cannula 122 penetrating skin 126 and a vein 128 at a puncture site 120. Under the normal flow condition, the outlet 124 of the cannula 122 delivers an infused fluid originating from the source of infused fluid 102 into the vein 128, whereupon the infused fluid is carried away by the flow of blood in the vein 128.

The source of infused fluid 102 is shown as a hanging bag or bottle, but may comprise a plurality of hanging bags or bottles, possibly in combination with flow controllers, pumps, check valves, drip chambers, tube mergers, connectors, ports, or other conventional infusion accessories, which are provided separately from the extravasation tester 100. The sight chamber 118 is a transparent tube or window through which fluid near the puncture site 120 may be visually or optically inspected. The sight chamber 118 may be a transparent portion of the cannula 122 or a transparent portion of the delivery tube 116 adjacent the puncture site 120. Components are not drawn to scale. For example, the sight chamber 118 is enlarged herein for ease of illustrating test results, and the source of infused fluid 102 is minimized to leave more room for showing the inventive elements. Fluid is allowed to flow freely in the delivery tube 116, and the sight chamber 118 contains fluid originating from the source of infused fluid 102, when the wheel 104 is centered over position 21, as shown in FIG. 4. In FIGS. 4, 5, 6, 7, and 8, position 21 is a representative point within the free-flow region 113. Movement of the wheel 104 is constrained by post pair 106 sliding in slot pair 110 as the wheel 104 is rolled or slid in either direction between ends 114 and 112.

Figure 5:
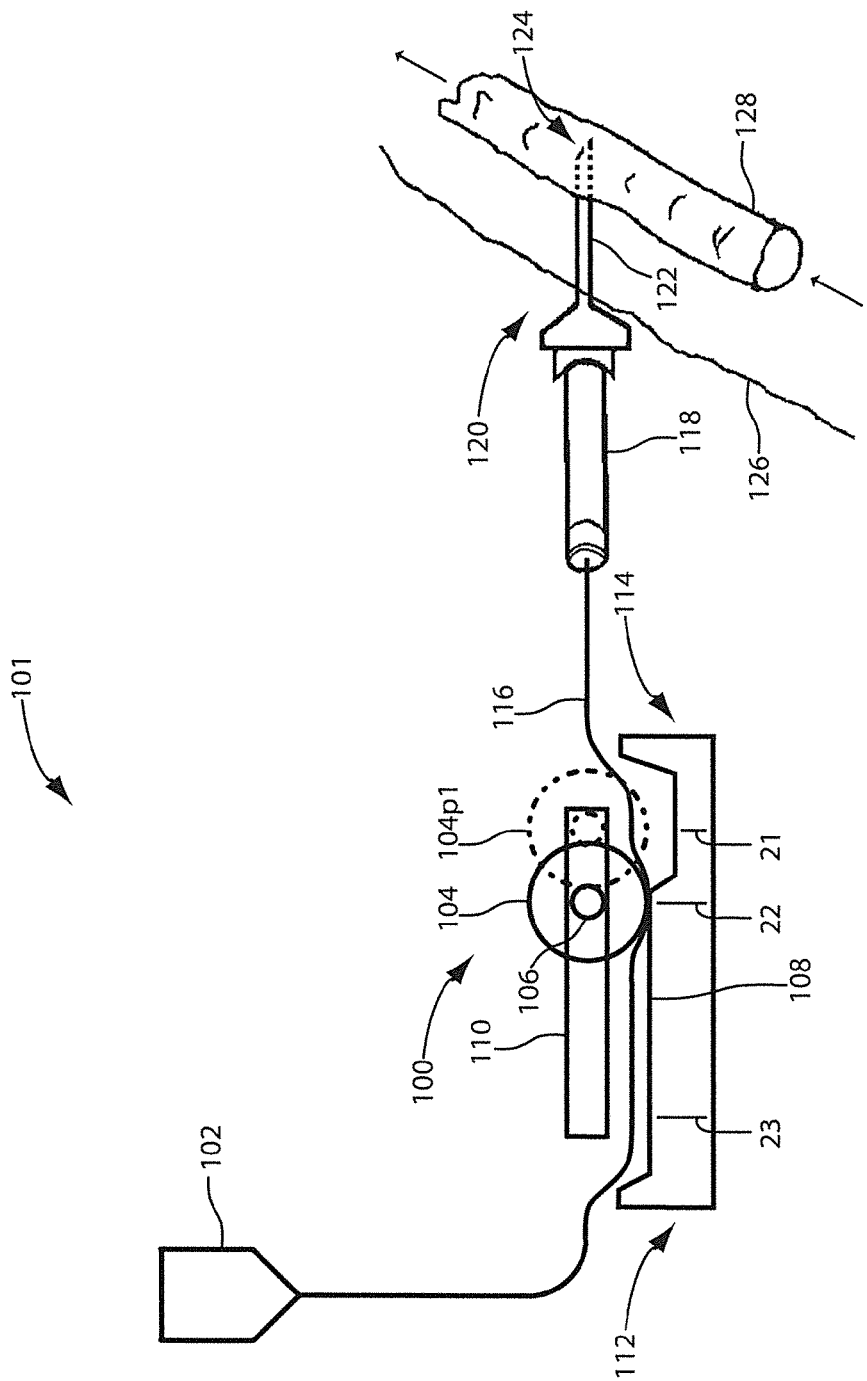
FIG. 5 is a schematic showing a first step of performing an extravasation test, for the case of a properly placed cannula.

FIG. 5 is a schematic illustrating a first step of performing an extravasation test, for the case of a cannula 122 properly placed inside the vein 128. In the first step of the extravasation test, the wheel 104 is rolled or slid out of the free-flow region 113 and into the tube-pinching region 111 by rolling or sliding the wheel 104 away from a phantom 104p1 centered over position 21 until the wheel 104 is centered over position 22. In FIGS. 4, 5, 6, 7, and 8, positions 22 and 23 and all positions in between are within the tube-pinching region 111. Position 22 corresponds to incipient flow cutoff, which occurs early in the wheel's 104 travel from end 114 to end 112.

At the end of the first step shown in FIG. 5 of the extravasation test, the flow in the delivery tube 116, sight chamber 118, and cannula 122 is stopped, because the delivery tube 116 is pinched closed between the wheel 104 and the platen 108, when the wheel 104 is moved and then left motionless over position 22. The sight chamber 118 contains fluid originating from the source of infused fluid 102, and the outlet 124 of the cannula 122 is surrounded by blood, the previously delivered fluid having been carried away by blood in the vein 128.

Figure 6:
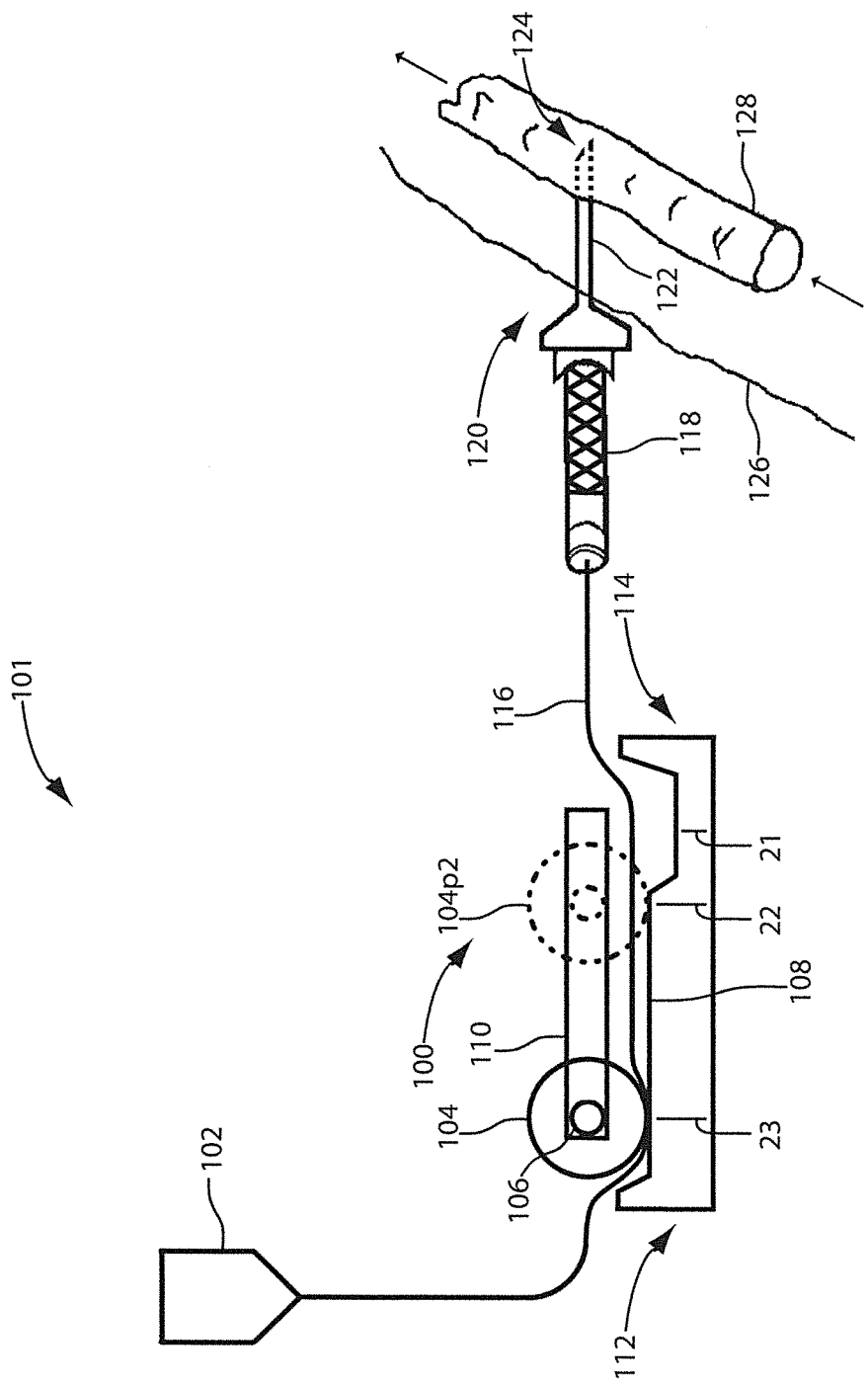
FIG. 6 is a schematic showing a second step of performing an extravasation test, showing the result obtained for the case of a properly placed cannula.

FIG. 6 is a schematic illustrating a second step of performing an extravasation test, showing the result obtained when the outlet 124 of the cannula 122 is properly placed inside the vein 128. In the second step of the extravasation test, the wheel 104 is rolled on the delivery tube 116 toward position 23, from a phantom 104p2 centered over position 22. The delivery tube 116 is pinched fully closed for all wheel positions between position 22 and position 23, inclusive, so that no flow is allowed past the point of tube closure between the wheel 104 and the platen 108. A test fluid, which in this case is blood, is withdrawn into the outlet 124 of the cannula 122 from the vein 128 when the flow in the delivery tube 116 is reversed by rolling the wheel 104 away from the puncture site 120 from position 22 toward position 23, and this reversed flow stops when the wheel 104 is stopped. A richly dark density of blood appears in the sight chamber 118 at the end of the second step of the extravasation test if the outlet 124 of the cannula 122 is properly placed inside the vein 128, and the withdrawn blood is shown by the crosshatched shading inside the sight chamber 118 in FIG. 6. If a richly dark density of blood appears in the sight chamber 118 before the wheel 104 reaches position 23, then the second step of the extravasation test may be concluded there. If a richly dark density of blood appears in the sight chamber 118 as the wheel 104 is rolled from position 22 toward position 23 or upon reaching position 23, then the extravasation test is said to be "passed", and the wheel 104 may be returned to position 21 in order to resume the infusion. Typically, the first and second steps of the extravasation test are performed by a single movement of the wheel 104 from position 21 toward position 23.

Fine control is afforded by the extravasation tester 100, and this fine control enables performance of a "passed" extravasation test with minimal incursion of blood into the cannula 122 and sight chamber 118. By choice of inner diameters of the delivery tube 116 and sight chamber 118, a ratio, of blood incursion distance in the sight chamber 118 to wheel 104 travel distance, can be made less than 1 or greater than 1, as desired. For example, if the inner diameter of the sight chamber 118 is made to be one half the inner diameter of the delivery tube 116, then the blood incursion in the sight chamber 118 moves an additional 4 millimeters per additional millimeter of movement of the wheel 104.

Figure 7:
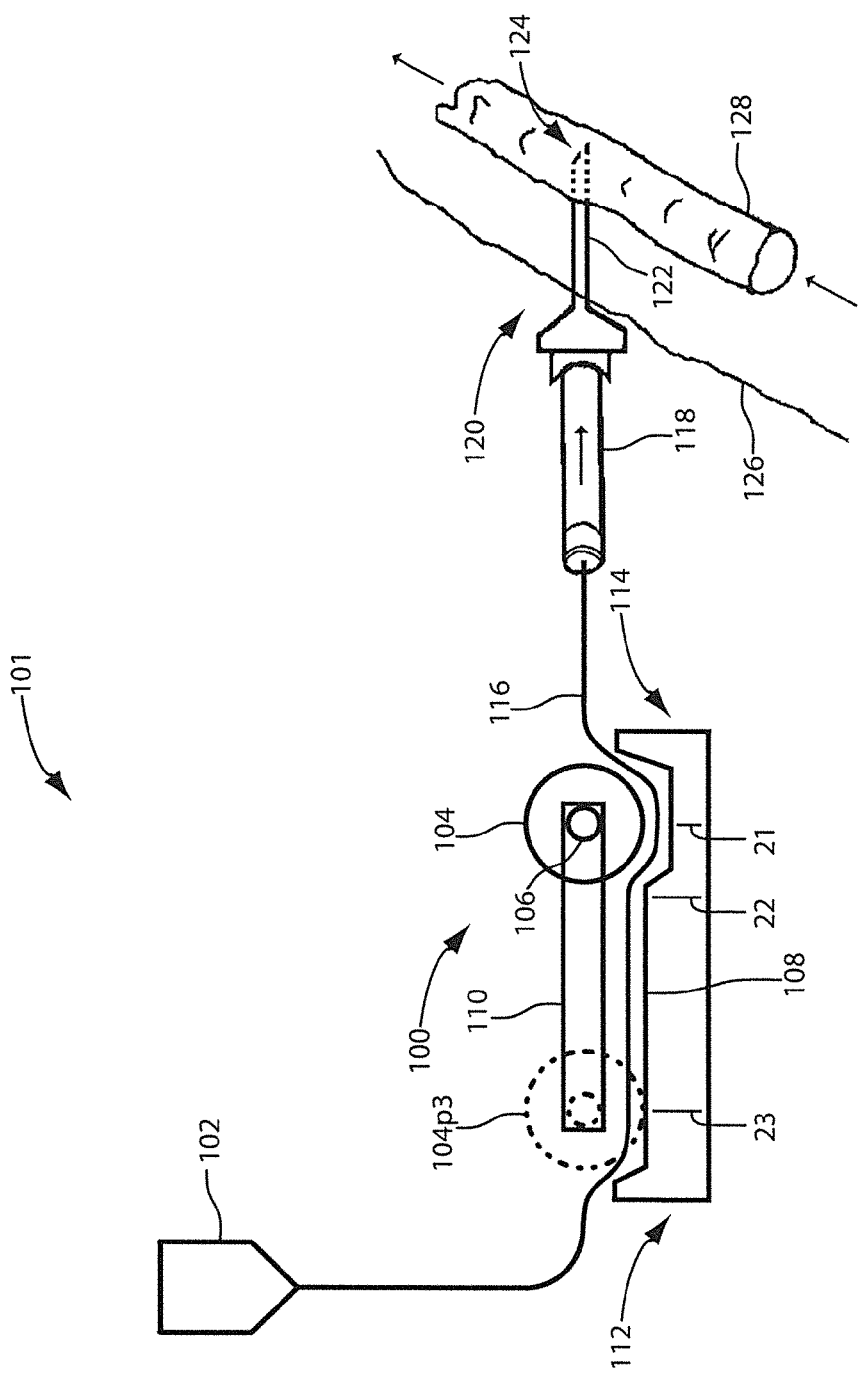
FIG. 7 is a schematic showing a return to the normal flow condition, for the case of a properly placed cannula.

FIG. 7 illustrates a return to normal flow, following a "passed" extravasation test, which indicates proper placement of the cannula 122 inside the vein 128. FIG. 7 illustrates the last of a sequence of steps shown in FIGS. 5, 6 and 7. When an extravasation test is "passed", the wheel 104 is returned to position 21 from a phantom 104p3 centered over position 23 in order to resume the infusion.

Figure 8:
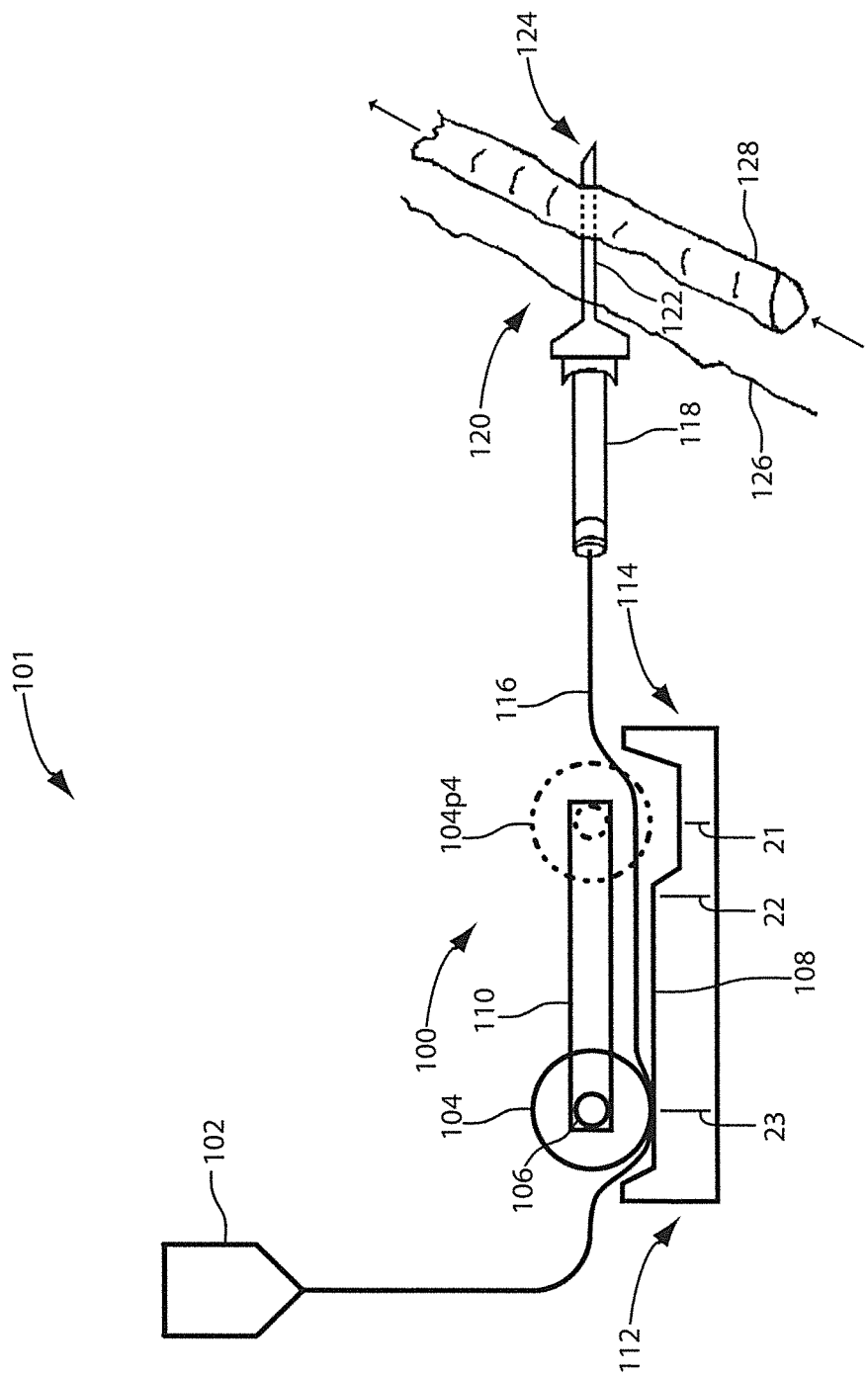
FIG. 8 is a schematic showing an extravasation test result obtained for the case of an improperly placed cannula.

FIG. 8 illustrates performance of an extravasation test, this time showing the result obtained when the outlet 124 of the cannula 122 is improperly placed, outside of the vein 128. When the outlet 124 of the cannula 122 is outside the vein 128, fluid originating from the source of infused fluid 102 accumulates around the outlet 124 of the cannula 122 instead of being carried away by flowing blood in the vein 128. When the wheel 104 is moved all the way to position 23, from a phantom 104p4 centered over position 21, a test fluid, comprising mostly or entirely the accumulated fluid originating from the source of infused fluid 102, is withdrawn back into the outlet 124 of the cannula 122. Little or no blood appears in the sight chamber 118 when the wheel 104 is rolled away from the puncture site 120 all the way to position 23 if the outlet 124 of the cannula 122 is outside the vein 128, and this is shown by the absence of shading inside the sight chamber 118 in FIG. 8. If little or no blood appears in the sight chamber 118 when the wheel 104 is rolled all the way to position 23, then the extravasation test is said to be "failed". In the case of a "failed" extravasation test, the delivery tube 116 is left in a fully closed state with the wheel 104 centered over position 23 or over any other position between positions 22 and 23 until a corrective action is performed. A corrective action may include one or more of the following: resetting of the cannula 122 in the vein 128 or in another vein, removal of the cannula 122 from the puncture site 120, replacement of the cannula 122 with another, establishing or re-establishing a proper flow condition, or ending the infusion.

The extravasation tester 100 can be mounted on the delivery tube 116 in a direction opposite the mounting direction shown in FIGS. 4, 5, 6, 7, and 8. For the case of an extravasation tester 100 having end 112 facing toward the puncture site 120, and end 114 facing toward the source of infused fluid 102, an extravasation test is performed by first moving the wheel 104 all the way from position 21 near end 114 to position 23 near end 112. Then the wheel 104 is rolled away from the puncture site 120, back from position 23 near end 112 toward the incipient flow cutoff point at position 22, thereby withdrawing a test fluid back into the outlet 124 of the cannula 122. If a richly dark density of blood appears in the sight chamber 118 before or upon reaching position 22, then the extravasation test is "passed", and the wheel 104 may be returned to position 21 in order to resume the infusion. If little or no blood appears in the sight chamber 118 upon reaching position 22, then the extravasation test is "failed", and the wheel 104 is left over position 22 or over any other position between positions 22 and 23 until a corrective action is performed.

The mounting direction of the extravasation tester 100 shown in FIGS. 4, 5, 6, 7, and 8 is preferred because this mounting direction is more intuitive, so that the extravasation tester 100 is easier to use. Furthermore, the mounting direction shown in FIGS. 4, 5, 6, 7, and 8 permits performance of a "passed" extravasation test with minimal incursion of blood into the cannula 122 and sight chamber 118, if the test is concluded when a richly dark density of blood appears in the sight chamber 118 before wheel 104 reaches position 23.

Having described our invention, we claim:

1. An extravasation tester, comprising:
   a frame having a hollow bore for receiving an intravenous infusion delivery tube;
   a platen on an inner surface of the hollow bore;
   a manually rotatable wheel having a circumferential outer surface and opposing axial posts; and
   opposing slots in the frame for receiving the opposing axial posts of the wheel so that the wheel is rotatable about its axis and translatable along the slots in the frame;
   wherein the slots and the inner surface of the hollow bore are configured so that:
   (a) when the wheel is in a free-flow region of the frame, the outer surface of the wheel does not pinch the delivery tube fully closed against the platen, so that a fluid in the delivery tube is allowed to flow in a forward direction,
   (b) when the wheel is in a tube-pinching region of the frame, the outer surface of the wheel pinches the delivery tube fully closed against the platen at a point of tube closure between the wheel and the platen, so that no flow is allowed in the delivery tube past the point of tube closure, wherein the tube-pinching region comprises a continuous range of more than one positions of the wheel at which the wheel pinches the delivery tube fully closed against the platen,
   (c) when the wheel is rolled on the delivery tube in the tube-pinching region of the frame, the point of tube closure translates along the delivery tube in conjunction with the rolling of the wheel, so that fluid in the delivery tube translates along the delivery tube in conjunction with the translation of the point of tube closure, whereby when the wheel is rolled in a reverse direction in the tube-pinching region of the frame, opposite the forward direction, the flow of the fluid in the delivery tube reverses with the reverse rolling of the wheel, and
   (d) wherein in the tube: pinching region, the slots are parallel to the platen, so that there is a constant clearance between the wheel and the platen when the wheel is in the tube-pinching region of the frame.

2. A method of performing an extravasation test, comprising the steps of:
   providing the extravasation tester of claim 1;
   manually rolling or sliding the wheel out of the free-flow region and into the tube-pinching region, thereby closing the delivery tube between the wheel and the platen;
   manually rolling the wheel on the delivery tube away from a puncture site, thereby withdrawing a test fluid from the puncture site and into a sight chamber; and
   performing the following, subject to the respective conditionals in each:
   (a) if a substantial concentration of blood is present in the sight chamber within or upon completion of the withdrawal of the test fluid into the sight chamber, returning the wheel to the free-flow region, and
   (b) if little or no blood is present in the sight chamber upon completion of the withdrawal of the test fluid into the sight chamber, leaving the delivery tube in a closed state until a corrective action is performed.

3. An intravenous infusion system, comprising:
   the extravasation tester of claim 1, mounted on the delivery tube;
   a source of an infused fluid;
   a cannula, intended for insertion into a vein at a puncture site; and
   the delivery tube, adapted for carrying the infused fluid from the source and toward the cannula.

4. The infusion system of claim 3, further including a sight chamber for viewing or detecting a test fluid withdrawn from the puncture site.

5. A method of performing an extravasation test, comprising the steps of:
   providing the extravasation tester of claim 1;

fully closing the delivery tube between the wheel and the platen by manually rolling or sliding the wheel out of the free-flow region and into the tube-pinching region;

reversing the flow of the fluid in the fully closed delivery tube by manually rolling the wheel on the delivery tube away from a blood vessel puncture site, thereby withdrawing a test fluid from the blood vessel puncture site and into a sight chamber; and performing the following, subject to the respective conditionals in each:
  (a) if a substantial concentration of blood is present in the sight chamber within or upon completion of the withdrawal of the test fluid into the sight chamber, returning the wheel to the free-flow region, and
  (b) if little or no blood is present in the sight chamber upon completion of the withdrawal of the test fluid into the sight chamber, leaving the delivery tube in a closed state until a corrective action is performed.

* * * * *